Figure 6:
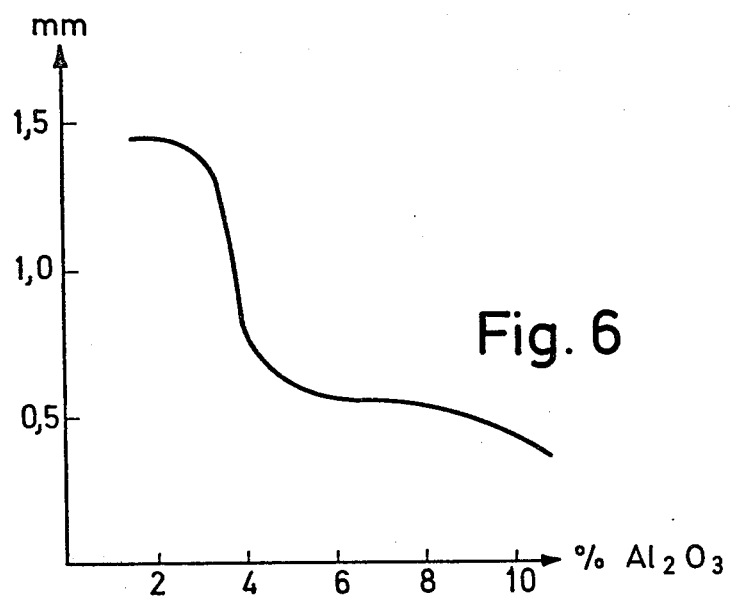

United States Patent [19]
Keller et al.

[11] 3,997,295
[45] Dec. 14, 1976

[54] PROCESS FOR THE DETERMINATION OF THE OXIDE CONTENT OF A MOLTEN SALT CHARGE

[75] Inventors: Rudolf Keller, Ossingen; Olaf Frei, Dachsen, both of Switzerland

[73] Assignee: Swiss Aluminium Ltd., Chippis, Switzerland

[22] Filed: Nov. 8, 1974

[21] Appl. No.: 521,957

[30] Foreign Application Priority Data
Nov. 13, 1973 Switzerland .................. 15912/73

[52] U.S. Cl. .............................................. 23/230 C
[51] Int. Cl.² ...................................... G01N 33/20
[58] Field of Search ............ 23/230 C, 253 C; 73/86
[56] References Cited
UNITED STATES PATENTS

| | | | |
|---|---|---|---|
| 2,174,053 | 9/1939 | Clarke | 23/230 C |
| 2,604,381 | 7/1952 | Hill | 23/230 C |
| 2,762,036 | 9/1956 | Triman | 23/253 C |
| 2,763,534 | 9/1956 | Campbell | 23/253 C |
| 3,002,820 | 10/1961 | Hall et al. | 23/230 C |

OTHER PUBLICATIONS

Cryolite, Properties and Industrial Application, Pennsylvania Salt Mfg. Co., 1952, pp. 11 and 12.

Primary Examiner—Robert M. Reese
Attorney, Agent, or Firm—Ernest F. Marmorek

[57] ABSTRACT

A process for determining the oxide content of a molten salt charge, in particular the aluminum oxide content of cryolite-based melts. The rate of dissolution of a test piece of a material which can dissolve in the melt is determined.

14 Claims, 7 Drawing Figures

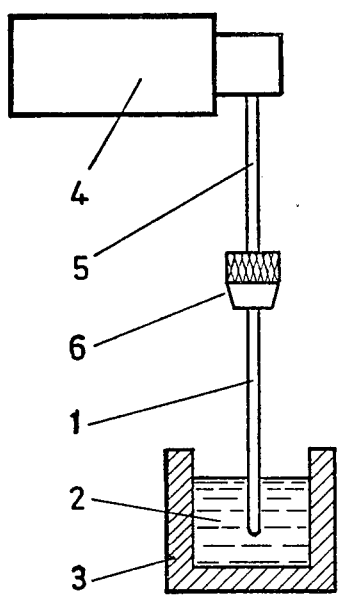
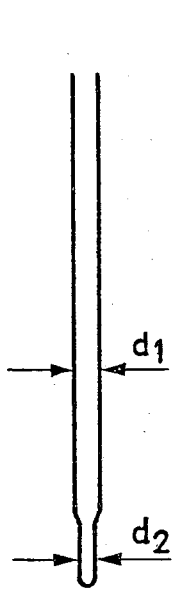
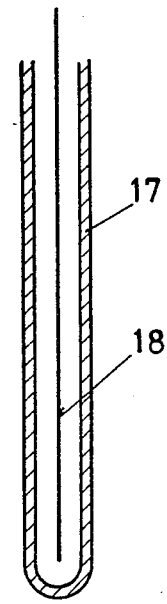
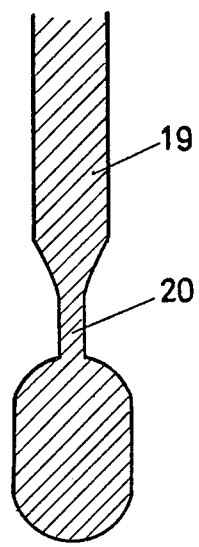
Fig. 1  Fig. 2  Fig. 4  Fig. 5
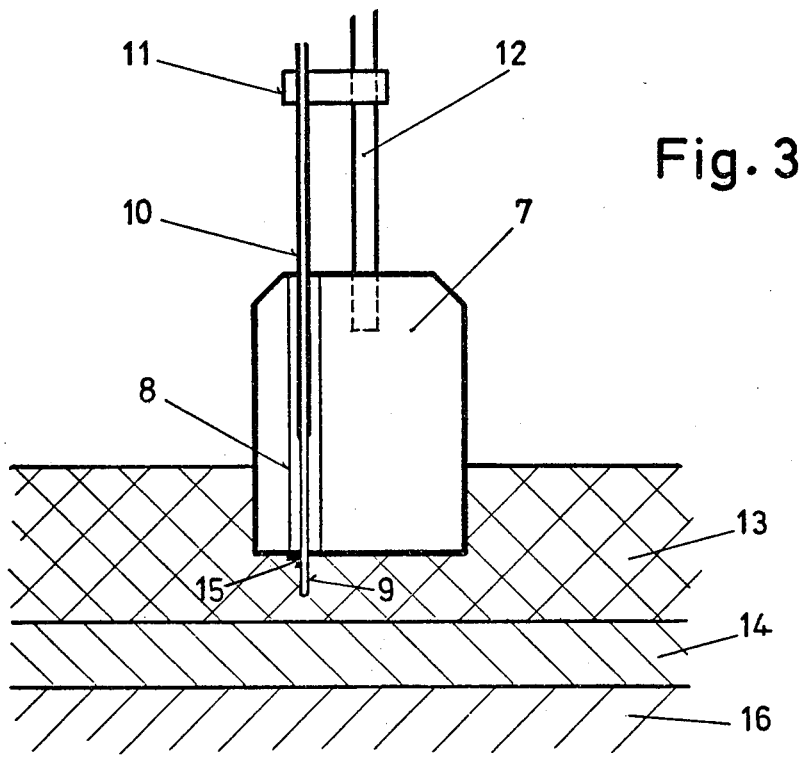
Fig. 3

PROCESS FOR THE DETERMINATION OF THE OXIDE CONTENT OF A MOLTEN SALT CHARGE

The invention concerns a process for the determination of the oxide content of a molten salt charge, in particular the determination of the $Al_2O_3$ content of a cryolite-based electrolyte by a simple determination of the rate of solution of solid oxide in such melts and concerns the use of this process for the determination of the amount of alumina to be added in the aluminum electrolysis.

In the normal electrolytic process for the production of aluminum, a cryolite-based melt containing dissolved $Al_2O_3$ is electrolysed at temperatures between 940° and 1000° C. The aluminum which separates out collects on the cathodic carbon bottom of the electrolyte cell, and carbon dioxide and monoxide gases form at the anodes. In this process $Al_2O_3$ is used up, and more has to be added to the electrolyte. If the $Al_2O_3$ concentration in the charge falls significantly then the current yield falls too, and then, at concentrations of around 1–2% $Al_2O_3$, the so-called anode effect which is evidenced by a large rise in voltage appears. If alumina is added to a bath which already contains a relatively large amount of $Al_2O_3$, the newly added $Al_2O_3$ does not readily dissolve, and this can lead to the formation of a harmful bottom sludge or crust.

In order to be able to make an optimal addition of $Al_2O_3$ and also to control certain other parameters connected with potline operation it is necessary to have some knowledge of the $Al_2O_3$ content of the electrolyte. A very small $Al_2O_3$ content can be easily recognized by the appearance of the anode effect. For higher contents it is necessary, at present, to carry out relatively high cost, and inconvenient, sampling and analyses.

For the main part therefore, in practice one has to do without such analyses. For automatic control of the reduction process at most only indirect, and not unambiguous, indications of the $Al_2O_3$ content are available. Thus for small $Al_2O_3$ contents even before the appearance of the anode effect there is such an indirect indication by way of a rise in the polarisation voltage. This characteristic voltage rise can be registered automatically and the process correspondingly adjusted. A rise in voltage, however, can result not only from a decrease in the alumina concentration but also through changes of another kind such as variations in the interpolar distance as a result of the matting of parts of the ridge of frozen electrolyte caused by a rise in the temperature of the pot. It would be of great value to have a measurement method for control purposes, which is independent of such interferences and thus is reliable also in such cases, and it is the object the invention to solve this problem.

The method according to the invention permits one to determine, with little expenditure, whether the $Al_2O_3$ content in the electrolysis cell is above or below a particular value, which is important for the operation of the pot and gives information therefore as to whether a little or a lot of $Al_2O_3$ should be added. It is therefore possible as a result of this to control the reduction process in such a way that the average $Al_2O_3$ concentration is closer to the optimum in particular with respect to the energy consumption. The method can be used not only in the traditional aluminum electrolysis process but also for processes in which inert anodes are used in the electrolysis of alumina.

Furthermore, the method can also be used with other electrolytic processes in which oxides are added as constituents of the electrolyte e.g. in the electrolytic production of beryllium. In general the invention can find application to determine the oxide content of salt melts, for example in cases where the solubility of the oxide is generally small but e.g. because of the effect it has on the corrosive properties of the melt, the amount of dissolved oxide is of great importance.

According to the invention, the rate of solution of test pieces which can dissolve in the melt is used as the measure of the oxide content in the electrolyte. For this test piece solid oxides or another suitable material can be used. This can be realized for example in a simple manner in which a rod or tube of a suitable solid oxide is dipped into the electrolyte and either the amount of oxide removed after a certain time or the time to remove a layer of oxide of certain thickness is measured. To increase the accuracy of measurement, the sample can be moved around in particular manner e.g. rotated at a known speed. Standardization is done by establishing a correlation between the amount removed and the oxide content, using melts of known concentration.

The invention is described in greater detail in the following with the aid of examples. The accompanying diagrams show:

FIG. 1 A device for the determination of a reference curve or for measuring the oxide contents in small quantities of salt melts.

FIG. 2 A test piece after a test

FIG. 3 An arrangement of the measuring equipment in which a test piece is passed through a hole in an anode of a cell for the electrolytic production of aluminum.

FIG. 4 A test piece which consists of a tube closed at the bottom and made of the material to be dissolved and having a conductor inside.

FIG. 5 A test piece with a characteristic, narrow region.

FIG. 6 A typical reference curve for a measurement in which is determined the reduction in diameter of a test rod in a specified time.

Figure 7:
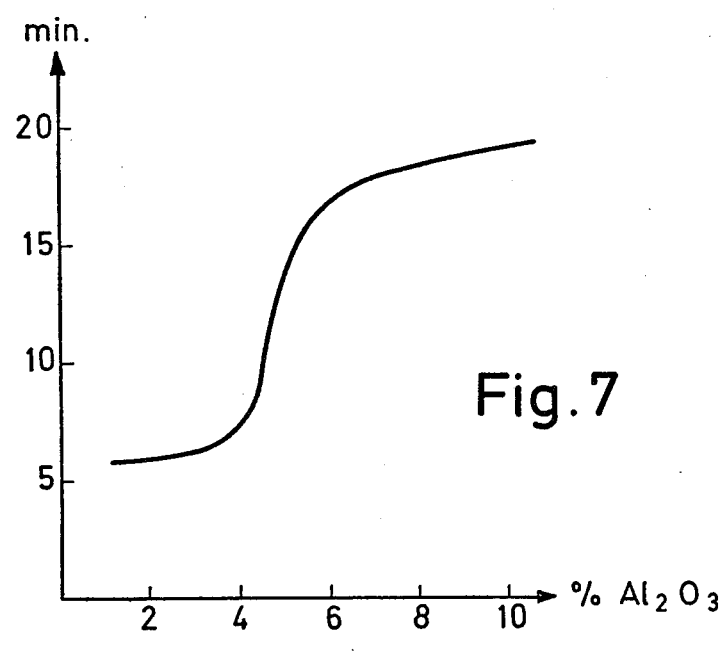

FIG. 7 A typical reference curve for a measurement in which is determined the time between immersion of a test tube in the melt and break-through of the wall of this test tube.

FIG. 1 shows a device for making measurement. A test rod 1 dips into the melt 2, which is kept in a container 3. The test rod is rotated by a motor 4 the axle of which is connected to the rod 1 via a coupling 6. After a certain time the test rod 1 is removed from the melt and has then the appearance shown in FIG. 2, i.e. its end has become thinner as a result of partial dissolution in the melt. The reduction in diameter from $d_1$ to $d_2$ is then measured after cleaning the rod, if this is necessary, and represents a measure for the oxide concentration in the melt, provided that the composition and temperature of the melt are known. In many cases it is possible to conclude, from a visual assessment of the amount of material removed, what the oxide concentration in the melt is. With some materials a change of appearance in the surface suffices to permit a valid judgement of the oxide content.

The measuring device shown in FIG. 1 is suitable, for standardization and determination purposes, for small quantities of molten salt melts. For determinations in larger quantities and for direct use in chemical systems such as in an electrolytic reduction cell for the production of aluminum, the device has to be modified accordingly. Thus, for example, a measuring cart, which can travel from cell to cell on the pot line, can be used to take measurements, the vehicle carrying on a holder, with or without facilities for rotation, a test rod which is introduced into the melt through a hole in the electrolyte crust. In another possible method the test rod, as is shown schematically in FIG. 3, is introduced through a hole through an anode. One of the pot anodes 7 is provided with a hole 8 for this purpose. The measuring probe which consists of the test rod 9 and an extension piece 10, is held firmly, by means of a securely mounted clamping device 11, onto the anode rod 12. If desired a device which permits rotation of the test rod can be used instead of the simple clamping device 11. In order to obtain a representative measure of the $Al_2O_3$ content in the electrolyte 13, it is useful to choose a place for measurement between the surface of the metal 14 and the bottom face of the anode 7 i.e. in the proper electrolyte layer. The electrolyte which enters the hole in the anode is namely low in oxide as a result of the electrolysis since this quantity of electrolyte is not continually replaced in adequate amounts. In order to determine the proper depth of immersion, the level of the metal or of the anode bottom can be determined. For this a separate measuring device can be employed or a projection 15 can be provided on the test rod to allow the lower face of the anode to be located. If the material is sufficiently resistant to attack by aluminum and if its electrical conductivity is so low that there is no danger of short circuiting between anode and cathode, then the end of the test rod can be lowered through the metal to the floor of the cell. The depth of immersion for the measuring probe can then is this case be determined in that the rod can be lowered until touching the carbon floor 16 of the cell and the rod can be left in this position or raised a few centimeters.

Instead of measuring the reduction in diameter of a test rod or tube, the time required to break through the wall of a tube or another hollow body can also be measured. If for example, as shown in FIG. 4, a tube 17 with the lower end closed and having a wire 18 inside is used, then the entrance of the melt upon breakthrough of the wall can be determined by means of a resulting electrical contact and registered via simple electrical instrumentation. The wall thickness of the hollow testing tube must be known, or at least the dissolution must take place in a characteristic manner at the place where the breakthrough occurs.

However some other kind of body, which exhibits characteristic properties of dissolution at least at one place, can also be used in FIG. 5 shows for example a test piece 19 which is tapered in a particular way at a position 20. In this case, by way of preference, the time required for breakthrough at the position 20 is measured; the moment of breakthrough can be recorded since a sudden corresponding loss of weight will be observed.

Another possibility is to immerse a suitable test piece in the electrolyte and to follow the change in weight continuously. The rate of weight loss is then characteristic of the $Al_2O_3$ content. In this way there is the possibility of following the consumption of $Al_2O_3$ continuously during the electrolysis process. Furthermore it is also possible to have the test piece in the form of a coating on another material e.g. as a glassy coating or as an electrochemically formed layer, and to observe the reduction of layer thickness or the removal of the layer. If an electrically insulating layer is applied to an electrically conductive material then the point in time, when contact is made between the melt and the substrate, can be taken as the point of registration.

There are materials in which, thanks to the heterogeneity of composition or structure, the appearance of the surface is changed by removal of part of the surface so that from a quick assessment of the appearance, it can be decided whether the amount removed from the test piece is large or small.

Materials which dissolve in a characteristic fashion and which are preferred for the test piece, are various solid oxides in the pressed or sintered state. Pure, sintered aluminum oxide and quartzglass have proved to be particularly good for use in cryolite melts as well as other ceramic materials containing aluminum oxide. Other test pieces or layers which come into consideration are those made of other ceramic or glassy oxides such as for example magnesium oxide, iron oxide, nickel oxide, other heavy metal oxides and also mixtures of various oxides such as e.g. porcelain, and also other materials such as halides, nitrides and carbides, for example, magnesium fluoride, aluminium nitride of silicon carbide.

In order that the results of the measurements are meaningful, the dissolution properties of the various test pieces or coatings which are to be compared, must be reproducible. Care must be taken therefore in the manufacture of the test piece. Thus, certain sintering conditions must be adhered to in the case of sintered oxides. If the time to break through is measured then the thickness of the material at the decisive point must be determined. If layers are dissolved away then they must be applied in a very reproducible manner.

EXAMPLE 1

For standardisation purposes between 2 and 10% $Al_2O_3$ was added to a mixture of 95% (weight percent) cryolite and 5% aluminum fluoride. Each mixture was melted in a graphite crucible and placed in a furnace at 1000° C. Commercially available, sintered $Al_2O_3$ rods 8 mm in diameter were immersed in the melt in accordance with the arrangement shown in FIG. 1, rotated at a speed of 75 revolutions per minute for 30 minutes and finally the amount removed from the rod (reduction in diameter) was determined as in FIG. 2. The dependence of the amount removed on the $Al_2O_3$ concentration shown in FIG. 6 was obtained from a series of such tests; the amount removed (reduction in diameter in mm) is plotted against the $Al_2O_3$ concentration in weight percent. One finds, surprisingly, that there are in general two (and only two) rates of solution which differ from each other by a factor of 3 viz., a high rate of solution (a removal of approx., 15 mm in 30 minutes) in the case of low $Al_2O_3$ contents, and a lower rate of solution (approx. 0.5 mm in 30 min) in the case of high $Al_2O_3$ contents. The transition is more or less discontinuous and lies between 3 and 4% $Al_2O_3$.

By making a measurement on a particular melt of unknown $Al_2O_3$ content the amount removed can now be measured on a rod of $Al_2O_3$ of the same properties and applied under the same conditions as in the calibration tests and from this measurement, using the above reference values it can be said whether the $Al_2O_3$ content of the melt lies above or below this transition region. In this example an immersion time of 30 minutes was chosen in order to ensure a certain degree of accuracy in the results. For a measurement under operating conditions, without question, a somewhat shorter time of immersion can be taken if corresponding reference values are obtained. It is also possible to shorten the measurement time by choosing a testing material prepared under different conditions e.g. different sintering conditions or of different composition.

EXAMPLE 2

In order to obtain a reference curve for a tube of quartz glass between 2 and 10% $Al_2O_3$ was added to a mixture of 95% cryolite and 5% Aluminium fluoride. The mixtures were melted in a graphite crucible and placed in an experimental furnace at 1000° C. A quartz glass (Vycor) tube, closed at the bottom and with a wall thickness of 1.3 mm, was dipped into this molten salt and the time until the melt breaks through the wall of the tube was measured; the moment when the breakthrough occurs was determined by making electrical contact between the wall of the crucible and a metal wire inside the quartz glass tube. The results from a series of measurements gave the relationship shown in FIG. 7. The time interval from immersion until breakthrough is given by the ordinate and the $Al_2O_3$ concentration in the melt, in weight percent, is given by the absissa. As can be seen from this reference curve the method of measurement is suitable to allow one to differentiate between an $Al_2O_3$ content of 4% or less, and an $Al_2O_3$ content of 6% or more. The time to breakthrough here lay between 6 and 20 minutes. In practice a test could be so arranged that for example the probe could be examined after 13 minutes to check whether breakthrough had occured or not. The time of measurement can be shortened accordingly by using a thinner-walled tube.

If such measurement is made in an aluminum electrolytic cell then it provides a measure of the $Al_2O_3$ content in the electrolyte in a short time. Thus a clear, safe indication of small $Al_2O_3$ contents is possible without waiting for the anode effect or for a chemical analysis of the electrolyte. If the result of the test shows that the $Al_2O_3$ content of the electrolyte is small and hence the $Al_2O_3$ dissolves readily in it, then a large addition of $Al_2O_3$ can be made or brought about by an automatic control of the process. Thus unnecessary anode effects can be avoided and the periods of low $Al_2O_3$ content during which unfavourable current yields occur, can be shortened. When the process is controlled automatically, the addition of excessive amounts of alumina can be avoided in those cases when the $Al_2O_3$ content is in fact high although the voltage behaviour indicate a low $Al_2O_3$ content.

What we claim is:

1. A method for determining the oxide content of a molten salt charge comprising the steps of providing test pieces composed of a substance which dissolves in the charge, said substance including at least one material chosen from the group consisting of metal oxides, metal halides, metal carbides, and metal nitrides;

determining a correlation between the rate of solution of said test piece and the content of oxide in said molten salt sample;

immersing at least partially, said test piece into the charge;

determining the rate of solution of said test piece in said charge; and thereafter determining the content of the oxide in the charge from the rate of solution of said test piece by means of the determined corrolation.

2. A method as claimed in claim 1, wherein said test piece is composed of the same oxide the content of which is to be determined in the charge.

3. A method, as claimed in claim 1, wherein said molten salt charge comprises cryolite and aluminum oxide.

4. A method, as claimed in claim 3, wherein the step of determining the rate of solution of said test piece comprises:

removing said test piece from said charge; and
measuring the amount of material removed from said test piece, by the melt.

5. A method, as claimed in claim 3, wherein the step of determining the rate of solution of said test piece further comprises:

measuring, continuously; the amount of material being removed from said test piece, by continuously monitoring the weight of said test piece.

6. A method as claimed in claim 3, wherein said test piece comprises a hollow body of predetermined thickness, and the step of determining the rate of solution of said test piece comprises measuring the time required for the molten salt to break through said body.

7. A process, as claimed in claim 3, wherein said test piece comprises a hollow body having a wall of predetermined thickness, and the step of determining the rate of solution of said test piece comprises:

determining whether or not the molten salt has broken through said wall after a predetermined time of immersion.

8. A method, as claimed in claim 3, wherein said test piece is in the form of a coating on a substrate and the step of determining the rate of solution of said test piece comprises:

determining the time for the molten salt to remove said coating from said substrate.

9. A method, as claimed in claim 3, wherein said test piece is in the form of a coating on a substrate and the step of determining the rate of solution of said test piece comprises:

determining whether or not the molten salt has removed said coating from said substrate.

10. A method, as claimed in claim 3, wherein said test piece is composed of a heterogeneous mixture of substances having different rates of solution from each other, and the step of determining the rate of solution of said test piece comprises:

removing said test piece from said charge after a predetermined time, and determining the rate of solution from the appearance of the test piece.

11. A method, as claimed in claim 3, wherein said test piece comprises a heterogeneous structure, and the step of determining the rate of solution of said test piece comprises:

removing said test piece from said charge after a predetermined time, and determining the rate of solution from the appearance of the test piece.

12. A method, as claimed in claim 3, wherein said test piece comprises a heterogeneous structure and is composed of a heterogeneous mixture of substances having different rates of solution from each other, and the step of determining the rate of solution of said test piece comprises:

removing said test piece from said charge after a predetermined time, and determining the rate of solution from the appearance of the test piece.

13. A method, as claimed in claim 3, wherein said test piece is composed of aluminum oxide.

14. A method, as claimed in claim 3, wherein said test piece is composed of silicon oxide.

* * * * *